(12) United States Patent
Fu et al.

(10) Patent No.: US 8,455,668 B2
(45) Date of Patent: Jun. 4, 2013

(54) METHOD FOR PREPARING HYDROXYMETHYLFURFURAL

(75) Inventors: Yao Fu, Hefei (CN); Jin Deng, Hefei (CN); Qingxiang Guo, Hefei (CN); Jing Zhao, Hefei (CN); Lei Liu, Hefei (CN)

(73) Assignee: University of Science and Technology of China (CN)

( * ) Notice: Subject to any disclaimer, the term of this patent is extended or adjusted under 35 U.S.C. 154(b) by 0 days.

(21) Appl. No.: 13/346,514

(22) Filed: Jan. 9, 2012

(65) Prior Publication Data

US 2012/0172607 A1    Jul. 5, 2012

Related U.S. Application Data

(63) Continuation of application No. PCT/CN2010/072850, filed on May 17, 2010.

(30) Foreign Application Priority Data

Jul. 9, 2009  (CN) .......................... 2009 1 0150079

(51) Int. Cl.
C07D 319/06 (2006.01)

(52) U.S. Cl.
USPC ......................................................... 549/372

(58) Field of Classification Search
USPC ................................................ 549/488, 372
See application file for complete search history.

(56) References Cited

U.S. PATENT DOCUMENTS

| 4,353,987 | A | 10/1982 | Wolf |
| 5,166,450 | A | 11/1992 | Avison et al. |
| 2007/0129553 | A1 | 6/2007 | Quaedflieg et al. |
| 2008/0033188 | A1 | 2/2008 | Dumesic et al. |

FOREIGN PATENT DOCUMENTS

| CN | 1821418 A | 8/2006 |
| CN | 101367783 A | 2/2009 |
| CN | 101456850 A | 6/2009 |
| CN | 101619051 A | 1/2010 |
| JP | 2000309590 A | 11/2000 |
| WO | 2004067524 A1 | 8/2004 |

OTHER PUBLICATIONS

Michael J. S. Dewar, Robert M. Riddle, "Factors Influencing the Stabilities of Nematic Liquid Crystals"; J. Am. Chem. Soc, (1975), 97, 6658-6662.
International Preliminary Report on Patentability and Written Opinion of the International Searching Authority; Application No. PCT/CN2010/072850; Issued: Jan. 10, 2012; 6 pages.
International Search Report; Application No. PCT/CN2010/072850; Issued; Jul. 13, 2010; Date Mailed: Aug. 19, 2010; 2 pages.
Z. Conrad Zhang et al., "Metal Chlorides in Ionic Liquid Solvents Convert Sugars to 5-Hydroxymethylfurfural"; Science., (2007), 316, 11 pages.
James A. Dumesic et al., "Production of Liquid Alkanes by Aqueous-Phase Processing of Biomass-Derived Carbohydrates"; Science., (2005), 308, 1446-1450.
Matsumoto. T, et al., "Selective Formation of Triose From Formaldehyde Catalyzed"; J.Am.Chem.Soc.,(1984), 106, 4829-4832.
Tim Sparey et al., "The Discovery of Fused Pyrrole Carboxylic Acids as Novel, Potent D-Amino Acid Oxidase (DAO) Inhibitors"; Bioorganic & Medicinal Chemistry Lett, (2008), 18, 3386-3391.
Edgar J. Witzemann., "The Isolation of Crystalline DL-Glyceric Aldehyde From Syrup Obtained by the Oxidation of Glycerol" J. Am. Chem. Soc., (1914), 36, 2223-2234.

*Primary Examiner* — Taofiq A Solola
(74) *Attorney, Agent, or Firm* — St. Onge Steward Johnston & Reens LLC

(57) ABSTRACT

A method for preparing hydroxymethylfurfural, which includes: a) mixing and dissolving triose or its derivatives and solvent 1 to obtain the first reaction mixture; b) reacting the obtained first reaction mixture with Alkaline Catalyst 1 to condense into hexose; c) mixing and dissolving the resulting hexose and solvent 2 to obtain the second reaction mixture; d) adding acid catalyst 2 to the second reaction mixture, then heating the second reaction mixture at 80~280° C. to form the third reaction mixture including hydroxymethylfurfural; e) obtaining the hydroxymethylfurfural separating by separating from the third mixture. The method is a new synthetic way for preparing 4-hydroxymethylfurfural and 5-hydroxymethylfurfural.

17 Claims, 8 Drawing Sheets

METHOD FOR PREPARING HYDROXYMETHYLFURFURAL

CROSS-REFERENCE TO RELATED APPLICATIONS

The present application is a continuation of pending International patent application PCT/CN2010/072850 filed on May 17, 2010 which designates the United States and claims priority from Chinese patent application 200910150079.5 filed on Jul. 9, 2009. The content of all prior applications is incorporated herein by reference.

FIELD OF THE INVENTION

The invention relates to a method for preparing a chemical raw material, particularly to a method for preparing hydroxymethylfurfural (HMF).

BACKGROUND OF THE INVENTION

Hydroxymethylfurfural (HMF) includes 4-hydroxymethylfurfural (4-HMF) and 5-hydroxymethylfurfural (5-HMF), both of which are multi-purpose intermediates, wherein 4-hydroxymethylfurfural (4-HMF) is a vital pharmaceutical intermediate. Cantharidins are an important class of anticancer drugs having a physiological function of inhibiting protein phosphatase. Cantharidins prepared from 4-hydroxymethylfurfural derivatives show inhibitory activity on PP2B with high selectivity (JP2000309590A). In addition, 4-hydroxymethylfurfural derivatives may also be used to prepare antagonists of prostaglandin receptor $EP_4$. $EP_4$ antagonists may be widely used to treat pain and a lot of other diseases (WO2004067524A1). 4-hydroxymethylfurfural may also be used to prepare antischizophrenic drugs (Tim Sparey, et al., Bioorganic & Medicinal Chemistry Lett, (2008), 18, 3386-3391). 4-hydroxymethylfurfural also has a potential use for synthesizing many useful compounds and new high molecular materials (particularly liquid crystal materials) (Michael J. S. Dewar, Robert M. Riddle, J. Am. Chem. Soc, (1975), 97, 6658-6662) including medicines, resin plastics, diesel fuel additives, etc. On the other hand, 5-hydroxymethylfurfural (5-HMF) may be used to synthesize many useful compounds and new high molecular materials, including medicines, resin plastics, diesel fuel additives, etc., by hydrogenation, oxidative dehydrogenation, esterification, halogenation, polymerization, hydrolyzation or other chemical reactions. Starting from 5-hydroxymethylfurfural (5-HMF), which is regarded currently as the most promising biomass platform molecule, a series of high-value-added products with great market prospect may be synthesized.

4-hydroxymethylfurfural (4-HMF) can only be prepared so far by modification of furan ring using butyl lithium and organosilicon reagents, wherein the reaction is carried out under severe conditions, and the reagents used are expensive. There have been no report to date on the preparation of 4-hydroxymethylfurfural from readily available and cheap chemical raw materials. Meanwhile, 5-hydroxymethylfurfural (5-HMF) is mainly prepared from fructose up to now (James A. Dumesic et al., Science., (2005), 308, 1446; US2008033188). However, fructose is not a rich resource in nature. It has been reported recently that 5-hydroxymethylfurfural (5-HMF) may be prepared from glucose, the most abundant natural carbohydrate (Z. Conrad Zhang et al., Science, (2007), 316, 1597). However, an expensive ionic liquid has to be used as a reaction solvent, and chloride(s) of metal chromium has to be used as a catalyst according to the method. In the above methods for preparing 5-hydroxymethylfurfural (5-HMF), the starting materials are all derived from sucrose or starch, the major food for human beings. As the food crisis goes from bad to worse, it is not an appropriate try to get rid of the oil crisis by manufacturing biofuel from food.

Therefore, it is necessary to find an abundant, readily available, cheap and renewable non-food biomass resource to prepare 4-hydroxymethylfurfural (4-HMF) and 5-hydroxymethylfurfural (5-HMF).

SUMMARY OF THE INVENTION

The embodiments of the invention provide a method for preparing hydroxymethylfurfural, in which hydroxymethylfurfural is prepared selectively at low cost from a starting material which is abundant, readily available and cheap, and mainly derived from renewable biomass.

The object of the invention is achieved via the following technical solution:

The embodiments of the invention provide a method for preparing hydroxymethylfurfural, comprising a. dissolving a triose or its derivative in Solvent 1 to obtain a first reaction mixture;

b. passing the first reaction mixture at a certain flow rate through a stationary catalyst bed loaded with Alkaline Catalyst 1 at a reaction temperature of −40~100° C., or adding Alkaline Catalyst 1 into the first reaction mixture to make a reaction occur under agitation at a temperature of −40~100° C., to obtain a hexose by condensation;

c. dissolving the condensation product hexose, in Solvent 2 to obtain a second reaction mixture;

d. passing the second reaction mixture at a certain flow rate through a stationary catalyst bed loaded with Acidic Catalyst 2 at a reaction temperature of 80~280° C., or adding Acidic Catalyst 2 into the second reaction mixture and heating the second reaction mixture comprising Acidic Catalyst 2 at a temperature of 80~280° C. which is sufficient to form hydroxymethylfurfural, to obtain a third mixture containing hydroxymethylfurfural; and e. subjecting the third mixture formed in step d to separation and purification by liquid-liquid extraction, or distillation under reduced pressure, or column chromatography to obtain hydroxymethylfurfural.

As can be seen from the technical solution provided by the above embodiments of the invention, in the embodiments of the invention, a triose or its derivative is used as the starting material which is subjected to catalytic condensation to obtain a hexose which is further subjected to catalytic dehydration to obtain hydroxymethylfurfural, wherein the obtained hydroxymethylfurfural is 4-hydroxymethylfurfural (4-HMF) or 5-hydroxymethylfurfural (5-HMF) or a mixture thereof. As this method is characterized by simple process, convenient preparation, easy separation as well as cheap and abundant starting material, i.e. triose, the manufacturing cost of hydroxymethylfurfural (HMF) is lowered effectively, a new synthesis route is established for 4-hydroxymethylfurfural (4-HMF), and the problem encountered in conventional methods for preparing 5-hydroxymethylfurfural (5-HMF) that the starting materials used are all derived from sucrose or starch, the major food of human beings, is avoided, so that the problem that the starting material for preparing 5-hydroxymethylfurfural (5-HMF) consumes food is alleviated.

DETAILED DESCRIPTION OF THE INVENTION

Figure 1A:
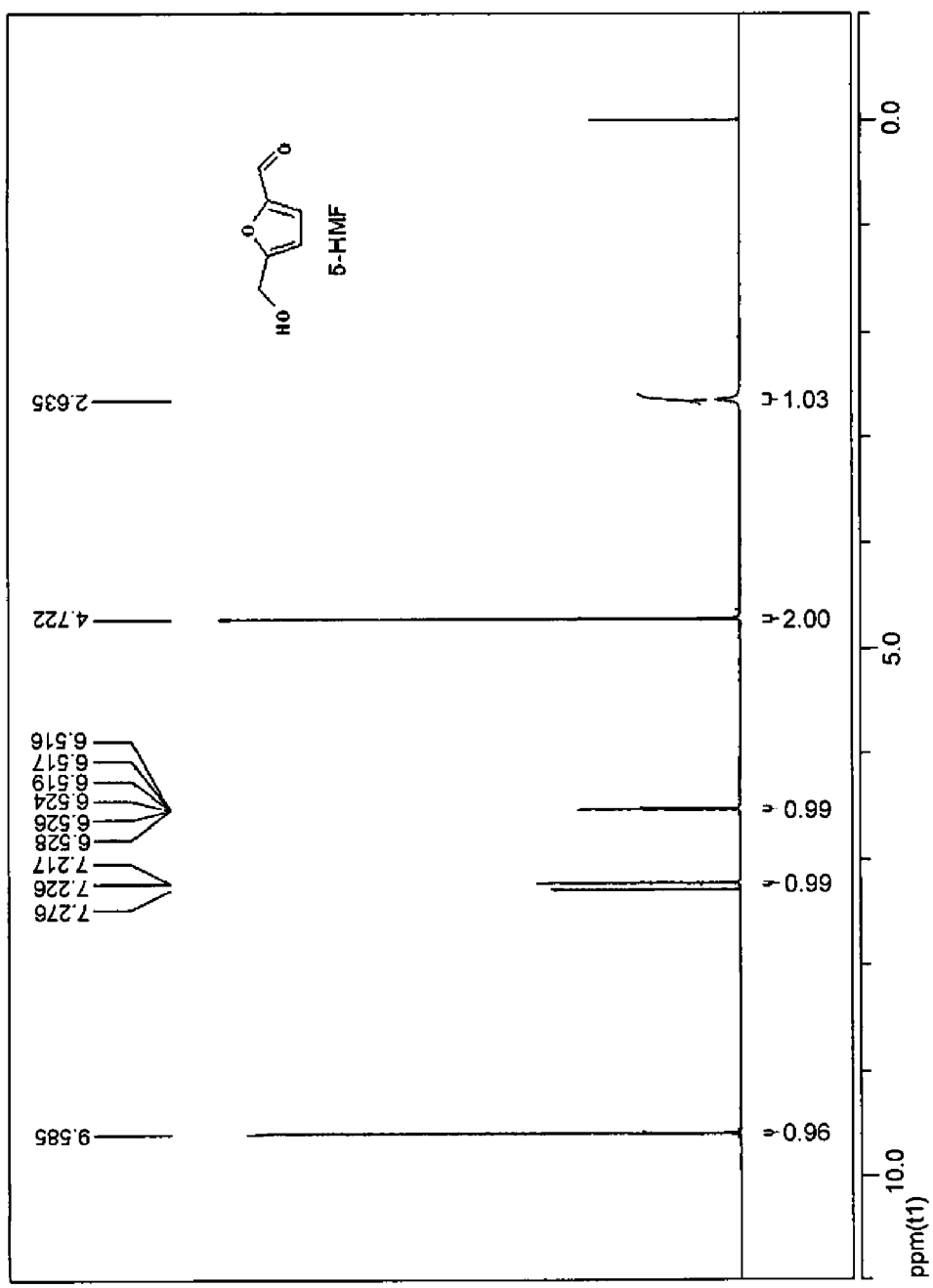
FIG. 1A is a $^1$H NMR spectrum of 5-hydroxymethylfurfural prepared according to an example of the invention.
Figure 1B:
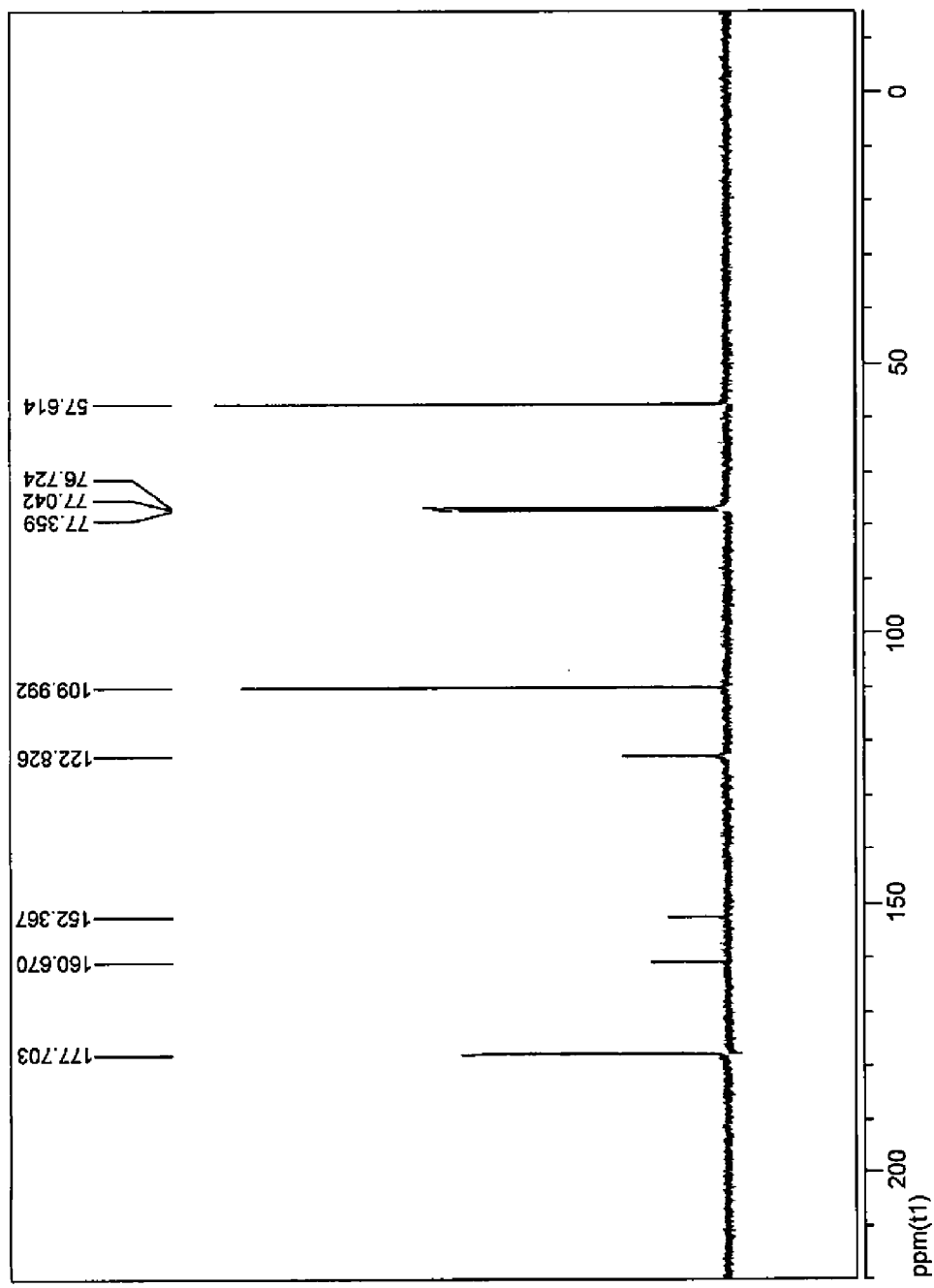
FIG. 1B is a $^{13}$C NMR spectrum of 5-hydroxymethylfurfural prepared according to an example of the invention.

The embodiments of the invention provide a method for preparing hydroxymethylfurfural, wherein the object of preparing hydroxymethylfurfural at low cost is achieved by using cheap and abundant triose or its derivative as the main starting material. The method comprises the following steps:

a. dissolving a triose or its derivative as a starting material in Solvent 1 to obtain a first reaction mixture;

b. using the first reaction mixture to prepare a hexose in a batch or continuous process, wherein Batch Process 1: adding Alkaline Catalyst 1 into the first reaction mixture and agitating at a certain temperature for a certain period of time to obtain a hexose via catalytic condensation; followed by removal of Alkaline Catalyst 1 from the obtained hexose by filtration; or addition of Acidic Catalyst 2 into the obtained hexose to neutralize Alkaline Catalyst 1; and removal of solvent 1 from the hexose if necessary; and Continuous Process 1: passing the first reaction mixture at a certain flow rate through a stationary catalyst bed loaded with Alkaline Catalyst 1 at a certain reaction temperature to a hexose via condensation; and removing Solvent 1 from the hexose if necessary;

c. adding the product of step a to Solvent 2 to obtain a second reaction mixture;

d. preparing a third reaction mixture containing hydroxymethylfurfural by using the second reaction mixture in a batch or continuous process, wherein Batch Process 2: adding Acidic Catalyst 2 into the second reaction mixture prepared in step c and agitating at a certain temperature for a certain period of time to form a third reaction mixture containing hydroxymethylfurfural; and Continuous Process 2: passing the second reaction mixture prepared in step c at a certain flow rate through a stationary catalyst bed loaded with Acidic Catalyst 2 at a certain reaction temperature to form a third reaction mixture containing hydroxymethylfurfural; and e. separating and purifying the third reaction mixture formed in step d by liquid-liquid extraction, or distillation under reduced pressure, or column chromatography to obtain hydroxymethylfurfural.

The method in an example of the invention involves catalytically condensing a triose or its derivative to produce a hexose, and then catalytically dehydrating the obtained hexose to produce hydroxymethylfurfural (HMF). Specifically, the method involves catalytically condensing ketotriose or its derivative to produce a branched hexose, and then catalytically dehydrating the obtained branched hexose to produce 4-hydroxymethylfurfural (4-HMF); or catalytically condensing aldotriose or its derivative to produce a linear hexose, and then catalytically dehydrating the obtained linear hexose to produce 5-hydroxymethylfurfural (5-HMF). Ketotriose used as the starting material in the method may be obtained from glycerine by chemical oxidation (US2007129553), biological fermentation (CN 1821418) or formaldehyde condensation (Matsumoto. T et al., J. Am. Chem. Soc., (1984), 106, 4829; U.S. Pat. No. 5,166,450). Aldotriose used as the starting material in the method may be obtained from glycerine by chemical oxidation (Edgar J. Witzemann., J. Am. Chem. Soc., (1914), 36, 2223) or biological fermentation (U.S. Pat. No. 4,353,987). Relevant reaction formulae are as follows:

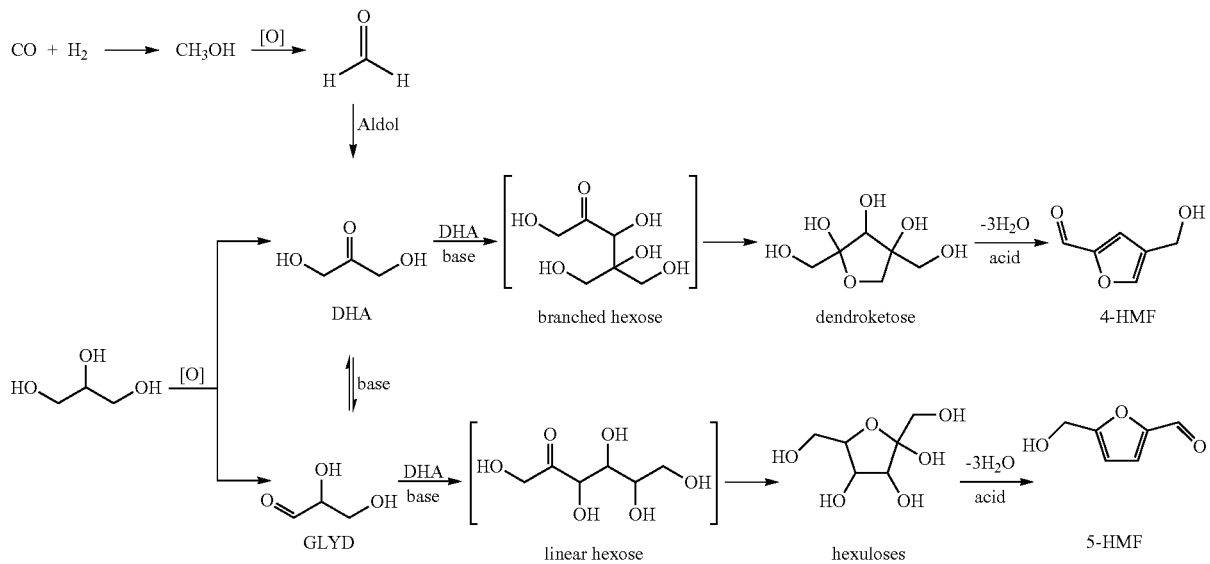

Glycerine is the main byproduct of biodiesel and may be obtained cheaply on a large scale. Meanwhile, formaldehyde is also a cheap staple chemical raw material that can be obtained from synthetic gas in large quantity. Therefore, this method reduces the manufacturing cost of 5-hydroxymethylfurfural greatly, and it has no impact on food resources. In other words, it avoids the problem in conventional methods for manufacturing 5-hydroxymethylfurfural, i.e., the conflict between the starting material for preparation and food crisis. The present invention also develops a novel synthesis route for 4-hydroxymethylfurfural. Furthermore, 4-hydroxymethylfurfural or 5-hydroxymethylfurfural may be prepared selectively by selecting corresponding starting materials.

To facilitate the understanding of the present invention, the process for carrying out the invention will be demonstrated in more detail with reference to the following specific examples.

Example 1

This example of the invention relates to a method for preparing hydroxymethylfurfural, wherein 4-hydroxymethylfurfural or 5-hydroxymethylfurfural may be prepared selectively by selecting different starting materials. The method comprises the following steps:

a. dissolving a triose or its derivative as the starting material in Solvent 1 capable of completely or partly dissolving the triose to obtain a first reaction mixture, wherein Solvent 1 is any one of water, dimethyl sulfoxide, dimethyl formamide, dimethyl acetylamide, methylene dichloride, tetrahydrofuran, 1,4-dioxane, N-methylpyrrolidinone, acetonitrile, cyclobutyl sulfone, trimethyl phosphate, ethyl acetate and ionic liquid, or any combination thereof; miscible solvents are selected where two or more solvents are combined to be used as Solvent 1; and the amount of Solvent 1 used is 0.5~100 times that of the triose starting material (the multiple relation is the ratio of the volume of Solvent 1 to the mass of the triose starting material);

b. condensing the first reaction mixture obtained in step a to obtain hexose by a batch or continuous process, wherein (1) Batch Process 1: adding Alkaline Catalyst 1 into the first reaction mixture obtained in step a and agitating at −40~100° C. to obtain a hexose via condensation, wherein Alkaline Catalyst 1 used herein is any one of Bronsted bases, Lewis bases, metal complexes, amino acids, solid bases and ion exchange resins or any combination thereof; in particular, these catalysts may include but not limited to sodium hydroxide, potassium hydroxide, calcium hydroxide, barium hydroxide, proline, homoproline, lysine, imidazolium bromide, thiazolium bromide, benzothiazolium bromide, solid bases, ion exchange resins, coordination compounds of Al, Zn, Ti, B, Si and Mn salts, etc.; wherein preferred Alkaline Catalyst 1 is a solid base or an anion exchange resin, such as 201×7 strongly basic anion exchange resin in the form of hydroxide ion and D201 strongly basic anion exchange resin in the form of hydroxide ion, with an anion exchange resin being preferred in practice for use as Catalyst 1; and the amount of Catalyst 1 used is 0.01~10 times that of the triose starting material (the ratio of the mass of Alkaline Catalyst 1 to the mass of the triose starting material); and (2) Continuous Process 1: passing the first reaction mixture at a certain flow rate (liquid hourly space velocity of 0.1~10.0 $h^{-1}$) through a stationary catalyst bed loaded with Alkaline Catalyst 1 at −40~100° C. to obtain a hexose via condensation; wherein Alkaline Catalyst 1 and the amount thereof used are the same as those used in the above Batch Process 1, and thus no repetition is made here; wherein anion exchange resin is also a preferred Catalyst 1 in Continuous Process 1 in practice;

c. mixing the condensation product of step b, hexose, with Solvent 2 to obtain a second reaction mixture; wherein the solvent miscible with the condensation product hexose is any one of dimethyl sulfoxide, dimethyl formamide, dimethyl acetylamide, N-methylpyrrolidinone, tetramethylurea, cyclobutyl sulfone, trimethyl phosphate, methyl propyl ketone and ionic liquid or any combination thereof; miscible solvents should be selected where two or more solvents are combined to be used as Solvent 2; the most preferred Solvent 2 is dimethyl sulfoxide, ionic liquid or their combination; and the amount of Solvent 2 used is 0.5~100 times that of the triose starting material (a ratio of the volume of Solvent 2 to the mass of the triose starting material);

d. preparing a third reaction mixture containing hydroxymethylfurfural in a batch or continuous process, wherein (1) Batch Process 2: adding Acidic Catalyst 2 into the second reaction mixture prepared in step c and heating the second reaction mixture at a temperature of 80~280° C. sufficient for the formation of hydroxymethylfurfural to obtain a third mixture containing hydroxymethylfurfural; wherein Acidic Catalyst 2 added in this step is any one of Bronsted acids, Lewis acids, metal complexes, solid acids, heteropoly acids and ion exchange resins, or any combination thereof; in particular, these catalysts may include but not limited to HCl, $H_2SO_4$, $H_3PO_4$, acetylpropionic acid, p-toluene sulfonatic acid, ammonium sulfate, pyridinium hydrochloride, $BF_3$, oxalic acid, solid acids, heteropoly acids, ion exchange resins, and coordination compounds of La, Al, Zn, Ti, Zr, Cr and Mn salts, etc.; and wherein preferred Catalyst 2 used is a solid acid or a cation exchange resin, for example, 001×7 strongly acidic anion exchange resin in hydrogen form, etc., with an cation exchange resin being most preferred; and the amount of Acidic Catalyst 2 used is 0.01~10 times that of the hexose (a ratio of the mass of Acidic Catalyst 2 to the mass of the hexose); and (2) Continuous Process 2: passing the second reaction mixture obtained in step c at a certain flow rate (liquid hourly space velocity of 0.1~10.0 $h^{-1}$) through a stationary catalyst bed loaded with Acidic Catalyst 2 at a reaction temperature of 80~280° C. to form a third reaction mixture containing hydroxymethylfurfural; wherein Acidic Catalyst 2 and the amount thereof added in this step are the same as those added in the above Batch Process 2, and thus no repetition is made here; wherein cation exchange resin is also a preferred Acidic Catalyst 2 in the Continuous Process 2 in practice; wherein, based on the foregoing processes, the process may further comprise a step of removing Catalyst 1 (anion exchange resin) added in the reaction of step b before step c by any known means, for example, filtration, centrifuge separation or decanting, etc.; and the process may further comprise a step of removing Solvent 1 in step a from the condensation product hexose before step c by any known means, for example, concentration under reduced pressure or freeze drying, etc.; and e. separating and purifying the third mixture formed in step d by liquid-liquid extraction, or distillation under reduced pressure, or column chromatography to obtain hydroxymethylfurfural.

Specifically, step e of the above method comprises:

Hydroxymethylfurfural obtained in the above preparation method refers to a single compound having structural feature (I) or (II), or a mixture thereof:

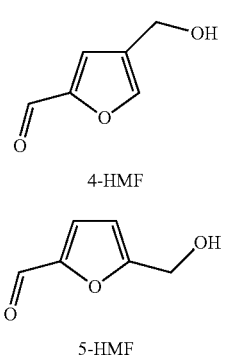

4-HMF

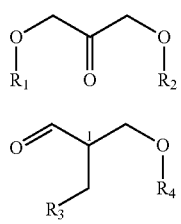

5-HMF

The triose or its derivative used in the above preparation method refers to a single compound having structural feature (III) or (IV), or a mixture thereof:

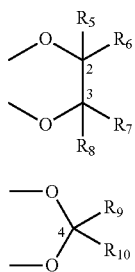

In the above formulae (III) and (IV), $R_1$, $R_2$, $R_3$ and $R_4$ each independently represents H, —PO(OH)$_2$, alkylcarbonyloxy containing 1~6 carbon atoms or alkyl containing 1~6 carbon atoms. Alternatively, $R_1$ and $R_2$ taken together and $R_3$ and $R_4$ taken together, represent ketal groups a-b; or $R_1$ and $R_2$ taken together or $R_3$ and $R_4$ taken together represents ketal group a-b, while each substituent in the other formula independently represents H, —PO(OH)$_2$, alkylcarbonyloxy containing 1~6 carbon atoms or alkyl containing 1~6 carbon atoms. $R_1$, $R_2$, $R_3$ and $R_4$ are further illustrated by the following structural feature (V), (V)

a b

In the above formula (V), $R_5$, $R_6$, $R_7$ and $R_8$ each independently represents H or alkyl containing 1~6 carbon atoms, and $R_9$ and $R_{10}$ each independently represents H or alkyl containing 1~6 carbon atoms. In addition, the chiral configuration of C1 in formula (IV) includes D-type, L-type and DL-type, while the chiral configurations of C2, C3 and C4 in formula (V) include D-type, L-type and DL-type.

In the above preparation method:

(1) where a single compound of triose or its derivative having the above structural feature (III) is used as the starting material in the above method for preparing hydroxymethylfurfural, the resulting product comprises predominantly the compound having structural feature (I) and a minor amount of the compound having structural feature (II) as a byproduct;

(2) where a single compound of triose or its derivative having structural feature (IV) is used as the starting material in the above method for preparing hydroxymethylfurfural, the resulting product comprises predominantly the compound having structural feature (II);

(3) where a mixture of a single compound of triose or its derivative having structural feature (III) and a single compound of triose or its derivative having structural feature (IV) is used as the starting material in the above method for preparing hydroxymethylfurfural, the resulting product comprises a mixture of the compound having structural feature (I), 4-hydroxymethylfurfural, and the compound having structural feature (II), 5-hydroxymethylfurfural.

In step a of the above preparation method, a single or mixed trioses or their derivatives may be mixed with Solvent 1 capable of dissolving triose completely or partly, with Solvent 1 capable of completely dissolving triose being preferred. In practice, Solvent 1 is preferably a single solvent, most preferably water. However, a combination of solvents may also be used on condition that the two or more solvents combined are miscible with each other, and the resulting solvent combination can dissolve triose, has no impact on the condensation reaction and is stable under reaction conditions.

In step b of the above preparation method, the hexose obtained by condensation of triose includes linear hexose and/or branched ketohexose, wherein the linear hexose includes any one or any combination of glucose, galactose, mannose, allose, altrose, gulose, talose, idose, fructose, sorbose, tagatose, psicose, ester derivatives of any one of these saccharides, ether derivatives of any one of these saccharides, optical isomers of any one of these saccharides, and optical isomers of any derivatives (ester derivatives and ether derivatives) of any one of these saccharides; and the branched hexose includes any one or any combination of dendroketose, ester derivatives of dendroketose, ether derivatives of dendroketose, optical isomers of dendroketose, optical isomers of ester derivatives of dendroketose and optical isomers of ether derivatives of dendroketose.

In step b of the above preparation method, the range of preferred reaction temperature varies with Solvent 1 and Alkaline Catalyst 1, wherein the reaction temperature is generally −40~100° C. In practice, where water is used as preferred Solvent 1 for the reaction and an anion exchange resin is used as preferred Alkaline Catalyst 1, the preferred temperature range is 0~60° C. While the reaction time for Batch Process 1 varies with reaction conditions and the desired yield, it is generally 10 minutes~48 hours. In practice, the reaction time is preferably 30 minutes-24 hours, and the reaction may be carried out under agitation. While the liquid hourly space velocity (LHSV) for Continuous Process 1 varies with reaction conditions and the desired yield, it is generally 0.5~5 h$^{-1}$. In practice, LHSV is preferably 1.0 h$^{-1}$.

In the above preparation method, where a single compound of triose or its derivative having structural feature (III) is used as the starting material, the ratio between compound 4-hydroxymethylfurfural having structural feature (I) and compound 5-hydroxymethylfurfural having structural feature (II) in the finally obtained products may be adjusted by changing reaction temperature. In more detail, raising the reaction temperature may increase the proportion of compound 4-hydroxymethylfurfural having structural feature (I) in the resulting products, while reducing the reaction temperature may increase the proportion of compound 5-hydroxymethylfurfural having structural feature (II) in the resulting products. For example, by changing the reaction temperature in the range of −40~100° C. in step b of the method, the ratio between compound 4-hydroxymethylfurfural having structural feature (I) and compound 5-hydroxymethylfurfural having structural feature (II) in the finally obtained products may be adjusted into 4-hydroxymethylfurfural:5-hydroxymethylfurfural=99:1~2:1. Specifically, (1) if the reaction temperature in step b is set to be −40~25° C., the ratio between compound 4-hydroxymethylfurfural having structural feature (I) and compound 5-hydroxymethylfurfural having structural feature (II) in the finally obtained products may be 4-hydroxymethylfurfural:5-hydroxymethylfurfural=99:1~9:1; (2) if the reaction temperature in step b is set to be 25~100° C., the ratio between compound 4-hydroxymethylfurfural having structural feature (I) and compound 5-hydroxymethylfurfural having structural feature (II) in the finally obtained products may be 4-hydroxymethylfurfural:5-hydroxymethylfurfural=9:1~2:1.

In addition, by changing the type of Alkaline Catalyst 1 in step b of the above preparation method, the ratio between compound 4-hydroxymethylfurfural having structural feature (I) and compound 5-hydroxymethylfurfural having structural feature (II) in the finally obtained products may also be adjusted, wherein the ratio may be 4-hydroxymethylfurfural:5-hydroxymethylfurfural=99:1~1:1.

In most cases, the reaction is faster at higher temperature, but higher selectivity is observed at lower temperature. At lower temperature, the reaction affords better yield, but it is too slow for practical use of the method. At higher temperature, the reaction is accelerated, but the selectivity becomes poor due to side reactions and product decomposition. Therefore, in order to maximize the yield of hexose, the reaction conditions should be optimized. That is, a temperature range should be selected such that the reaction is fast enough while satisfied yield is obtained.

Where insoluble Alkaline Catalyst 1 is used in Batch Process 1 in step b of the above preparation method, Alkaline Catalyst 1 may be removed from the reaction mixture before the subsequent step c. That is, Alkaline Catalyst 1 may be removed from the condensation product hexose by any known means, for example, filtration, centrifuge separation or decantion, etc. After removal, an additional amount of original solvent may be used to wash Alkaline Catalyst 1, and Alkaline Catalyst 1 may be further washed with 50% acetic acid solution. Then, the washing solution and the filtrate are combined to minimize the loss of the resulting hexose filtrate.

The above method may also comprise a step of removing Solvent 1 from the condensation product hexose obtained in step b before step c, such as, in the case that Solvent 1 has to be removed (for example, when Solvent 1 (e.g. water) selected in the first reaction stage (step a) is not a preferred solvent for use as Solvent 2 in the second reaction stage (step c), Solvent 1 may be removed before step c; if Solvent 1 (e.g. dimethyl sulfoxide) selected in the first reaction stage (step a) is also a preferred solvent for use as Solvent 2 in the second reaction stage, it is not necessary to remove Solvent 1). Solvent 1 contained in the mixture solution of hexose may be removed by any known means, for example, concentration under reduced pressure or freeze drying, with no necessity for further separation and purification.

Where soluble Alkaline Catalyst 1 is used in Batch Process 1 in step b, excessive Alkaline Catalyst 1 may be neutralized by adding a solid acid or a strongly acidic ion exchange resin before the subsequent step c, and then a subsequent reaction may be carried out.

In step d of the above preparation method, the preferred range of reaction temperature varies with Solvent 2 and Acidic Catalyst 2, wherein the reaction temperature is generally 80~280° C., preferably 100~180° C. The reaction time of Batch Process 2 is generally 1~48 hours, preferably 3~8 hours. The reaction may also be carried out under agitation. While the liquid hourly space velocity (LHSV) for Continuous Process 2 varies with reaction conditions and desired yield, it is generally 1~6 h$^{-1}$. In practice, LHSV is preferably 2.0 h$^{-1}$.

When an ionic liquid is used as Solvent 2 in step c for obtaining the second reaction mixture by mixing and dissolution, hydroxymethylfurfural may be obtained in step e of the above preparation method from the third mixture containing hydroxymethylfurfural by liquid-liquid extraction or distillation under reduced pressure, wherein the extracting agent is an organic solvent immiscible with the ionic liquid system and may be any one or any combination of ethyl acetate, ethyl ether, methylene dichloride and chloroform.

When a non-ionic liquid is used as Solvent 2 in step c for obtaining the second reaction mixture by mixing and dissolution, hydroxymethylfurfural may be obtained from the third mixture containing hydroxymethylfurfural by distillation under reduced pressure, or column chromatography.

According to the preparation method in the embodiments of the invention, when a ketotriose or its derivative having the above structural feature (III) is used as the starting material, the ketotriose or its derivative is catalytically condensed to give a branched hexose which is catalytically dehydrated to give 4-hydroxymethylfurfural (4-HMF); when an aldotriose or its derivative having the above structural feature (IV) is used as the starting material, the aldotriose or its derivative is catalytically condensed to give a linear hexose which is catalytically dehydrated to give 5-hydroxymethylfurfural (5-HMF); and when a mixture of a ketotriose or its derivative having the above structural feature (III) and an aldotriose or its derivative having the above structural feature (IV) is used as the starting material, the mixture of the ketotriose or its derivative and the aldotriose or its derivative is catalytically condensed to give hexoses which are catalytically dehydrated to give a mixture of 4-hydroxymethylfurfural and 5-hydroxymethylfurfural (5-HMF). This method may be used to prepare 4-hydroxymethylfurfural or 5-hydroxymethylfurfural selectively by changing the starting material.

For clearer illustration of the succeeding examples, short notations are given for the materials in various examples wherein like short notation used anywhere refers to like content exclusively. Specifically, the following short notations are used:

| | |
|---|---|
| DMSO | dimethyl sulfoxide |
| 4-HMF | 4-hydroxymethylfurfural |
| 5-HMF | 5-hydroxymethylfurfural |
| GLYD | glyceraldehyde |
| DHA | 1,3-dihydroxyactone |
| 001×7resin | 001×7 strongly acidic ion exchange resin (H form) |
| 201×7resin | 201×7 strongly basic ion exchange resin (OH form) |
| D201resin | D201 macroporous strongly basic ion exchange resin (OH form) |
| D202resin | D202 macroporous strongly basic ion exchange resin(OH form) |
| IRA-400 | Amberlite® IRA-400 strongly basic ion exchange resin (OH form) |
| IRA-402 | Amberlite® IRA-402 strongly basic ion exchange resin (OH form) |
| IRA-410 | Amberlite® IRA-410 strongly basic ion exchange resin (OH form) |
| IRA-900 | Amberlite® IRA-900 macroporous strongly basic ion exchange resin (OH form) |
| IRA-120 | Amberlite® IRA-120 strongly acidic ion exchange resin (H form) |
| IRA-200 | Amberlite® IRA-200 macroporous strongly acidic ion exchange resin (H form) |
| Amberlyst-15 | Amberlyst® 15 macroporous strongly acidic ion exchange resin (H form) |
| HPLC | liquid chromatography (for determination of the content of hydroxymethylfurfural (HMF) as well as the ratio between 4-HMF and 5-HMF in a reaction solution) |

Example 2

This example provides a method for preparing hydroxymethylfurfural, particularly a method for preparing 5-hydroxymethylfurfural (5-HMF) using DL-glyceraldehyde (DL-GLYD) as the starting material. The method is detailed as follows:

DL-GLYD (0.3682 g) with purity of 90% was dissolved in deionized water (4 mL), and Amberlite® IRA-410 strongly basic ion exchange resin (OH form, 0.4 g) was added in the resulting solution. The reaction was allowed to proceed at 5.0° C. under agitation for 12 hours, followed by filtration. The resin was washed with a small amount of water and 50% acetic acid solution, and the washing solution was combined with the filtrate. The filtrate was concentrated to dry under reduced pressure. To the concentrate were added DMSO (2 mL) and Amberlyst® 15 strongly acidic ion exchange resin (H form, 0.2 g). The resulting mixture was allowed to react at 110° C. under agitation for 5 hours, after which HPLC analysis showed that the molar yield of 5-HMF was 71.38% (based on D-GLYD). FIGS. 1a (solvent: CDCl$_3$, 400 MHz) and 1b (solvent: CDCl$_3$, 100 MHz) show the $^1$H NMR spectrum and $^{13}$C NMR spectrum of the resulting 5-hydroxymethylfurfural (5-HMF).

Example 3

Figure 2A:
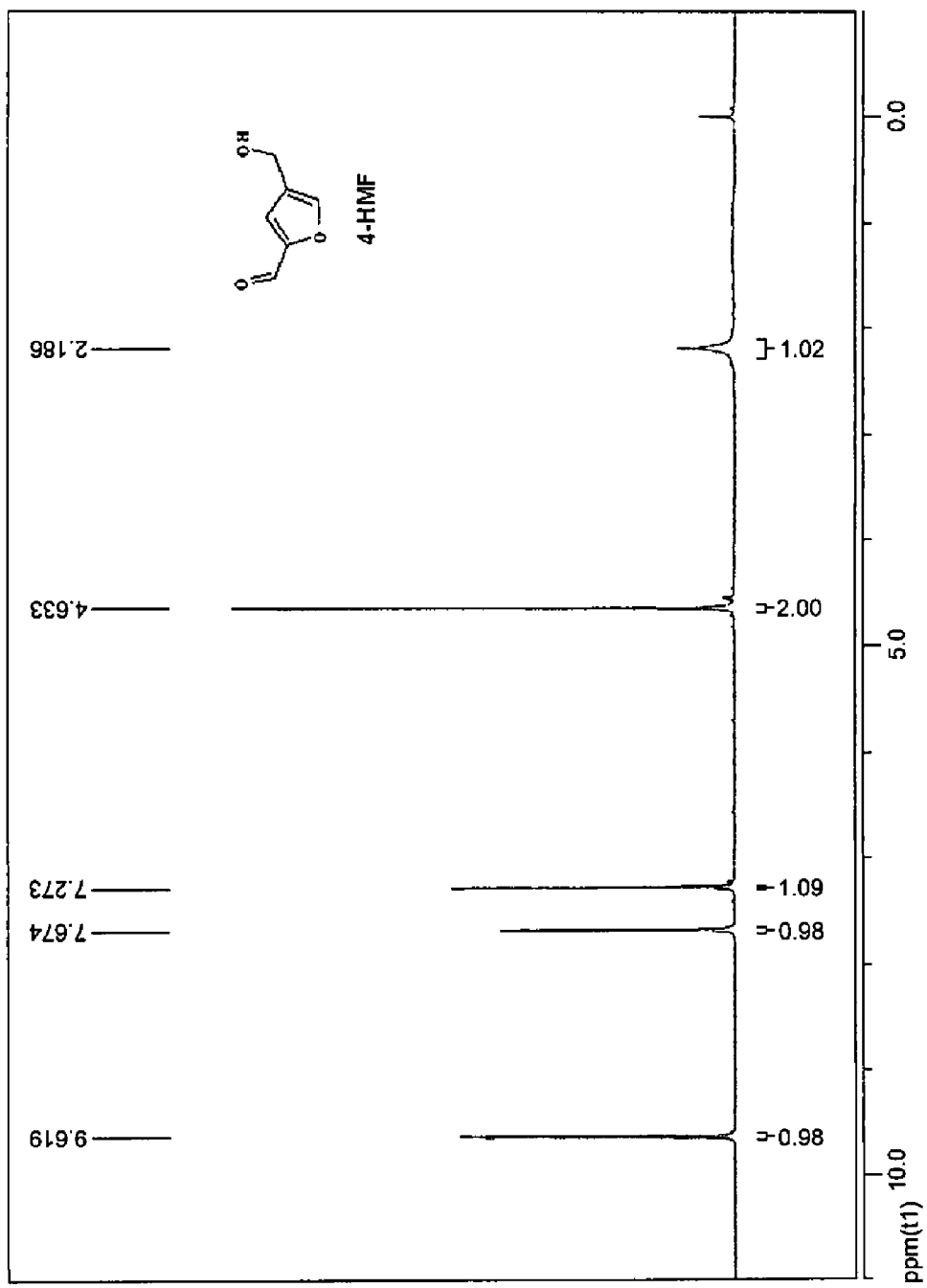
FIG. 2A is a $^{1}$H NMR spectrum of 4-hydroxymethylfurfural prepared according to an example of the invention.
Figure 2B:
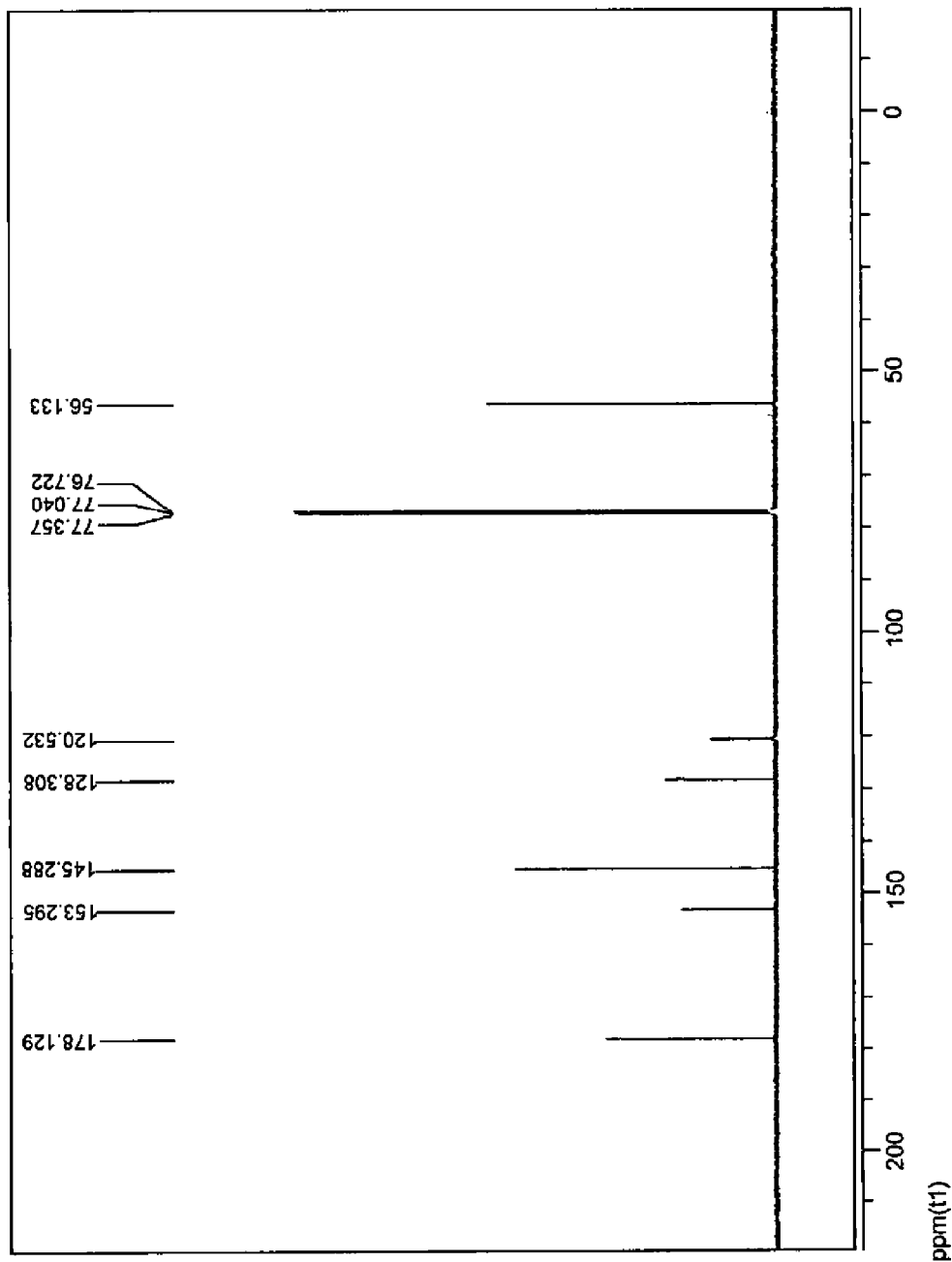
FIG. 2B is a $^{13}$C NMR spectrum of 4-hydroxymethylfurfural prepared according to an example of the invention

This example provides a method for preparing hydroxymethylfurfural, particularly a method for preparing 4-hydroxymethylfurfural (4-HMF) using 1,3-dihydroxyactone (DHA) as the starting material. The method is detailed as follows:

DHA (0.4016 g) with purity of 95% was dissolved in deionized water (4 mL), and Amberlite® IRA-410 strongly basic ion exchange resin (OH form, 0.4 g) was added in the resulting solution. The reaction was allowed to proceed at 0.0° C. under agitation for 24 hours, followed by filtration. The resin was washed with a small amount of water and 50% acetic acid solution, and the washing solution was combined with the filtrate. The filtrate was concentrated to dry under reduced pressure. To the concentrate were added DMSO (2 mL) and Amberlyst® 15 strongly acidic ion exchange resin (H form, 0.2 g). The resulting mixture was allowed to react at 110° C. under agitation for 5 hours, after which HPLC analysis showed that the molar yield of 4-HMF was 80.95% (based on DHA), the molar yield of 5-HMF was 4.15% (based on DHA), and 4-HMF: 5-HMF=95.12%:4.88%. FIGS. 2a (solvent: CDCl$_3$, 400 MHz) and 2b (solvent: CDCl$_3$, 400 MHz) show the $^1$H NMR spectrum and $^{13}$C NMR spectrum of the resulting 4-hydroxymethylfurfural (4-HMF).

Examples 4~8

Figure 3A:
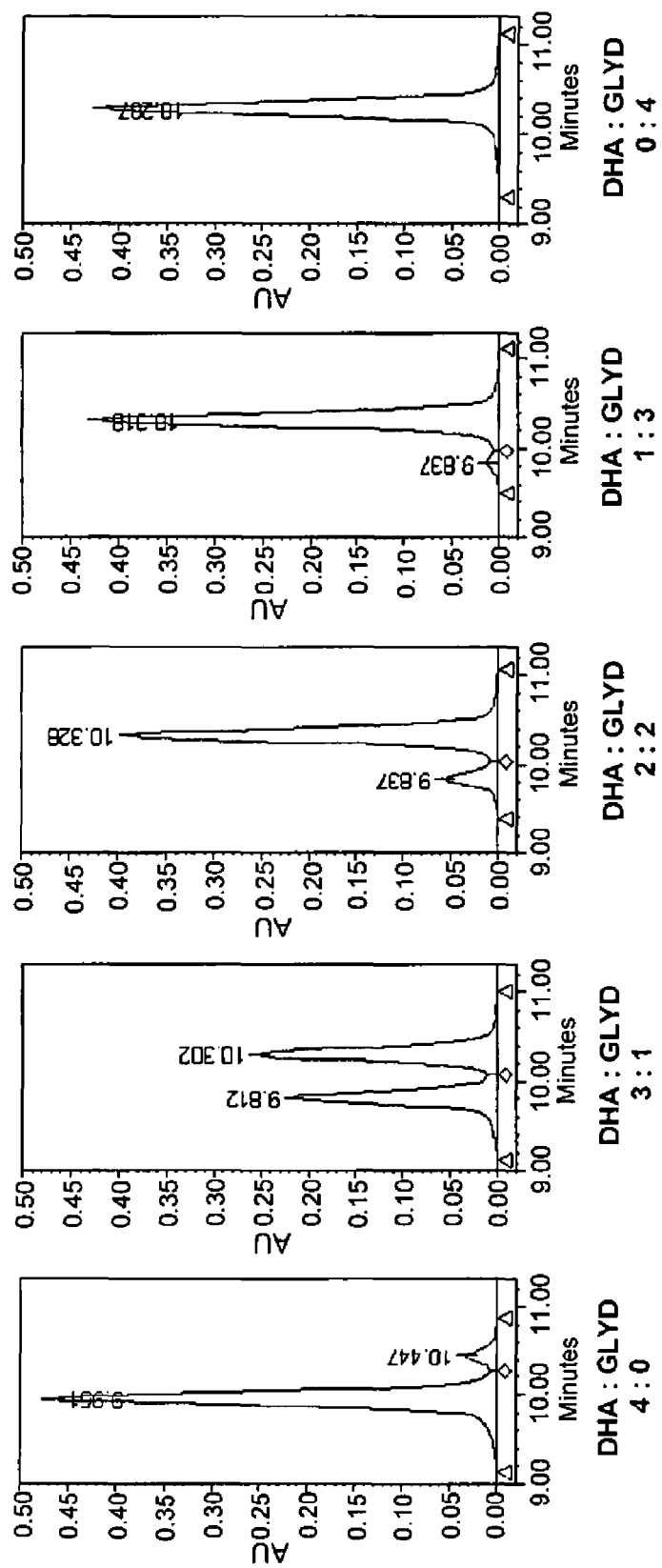
FIG. 3A is liquid chromatography (HPLC) spectra of HMF prepared from mixtures of 1,3-dihydroxyacetone (DHA) and glyceraldehyde (GLYD) of varying ratios according to an example of the invention.
Figure 3B:
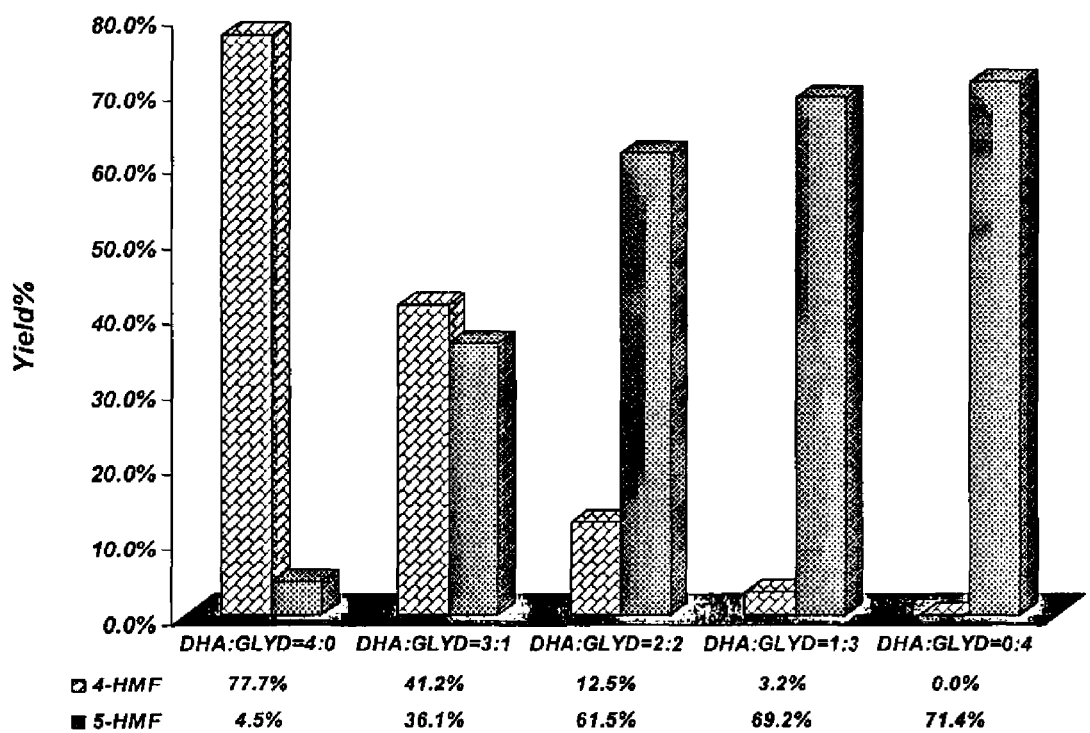
FIG. 3B is a chart showing the data reflecting the influence of mixing ratio of the starting materials on product composition ratio according to an example of the invention.

These examples involve preparation of 4-hydroxymethylfurfural (4-HMF) and 5-hydroxymethylfurfural (5-HMF) using mixtures with varying ratios of DL-glyceraldehyde (DL-GLYD) and 1,3-dihydroxyacetone (DHA). The details are as follows:

The preparation procedure was basically the same as in the above examples, except that DL-GLYD in Example 2 was replaced by mixtures formed by mixing DL-GLYD and DHA in various ratios (see Table 1 below). The specific operating parameters were shown in Table 1. HPLC spectra were shown in FIG. 3a, and HMF yields and product composition ratios were shown in FIG. 3b.

TABLE 1

Preparation of HMF from mixtures of DL-glyceraldehyde (DL-GLYD) and 1,3-dihydroxyacetone (DHA) in various ratios

| Example | DHA (95%)/g | DL-GLYD (90%)/g | IRA402 Resin/g | Water/ mL | Reaction temperature/ ° C. | Reaction time/h | DMSO/ mL | Amberlyst-15 resin/g | Reaction temperature/ ° C. | Reaction time/h | HMF Yield/ % | 4-HMF:5-HMF |
|---|---|---|---|---|---|---|---|---|---|---|---|---|
| 4 | 0.4123 | — | 0.4 | 4 | 5 | 12 | 2 | 0.2 | 110 | 5 | 82.12 | 95:5 |
| 5 | 0.3093 | 0.0921 | 0.4 | 4 | 5 | 12 | 2 | 0.2 | 110 | 5 | 77.33 | 53:47 |
| 6 | 0.2062 | 0.1841 | 0.4 | 4 | 5 | 12 | 2 | 0.2 | 110 | 5 | 73.96 | 17:83 |
| 7 | 0.1031 | 0.2762 | 0.4 | 4 | 5 | 12 | 2 | 0.2 | 110 | 5 | 72.37 | 4:96 |
| 8 | — | 0.3682 | 0.4 | 4 | 5 | 12 | 2 | 0.2 | 110 | 5 | 71.38 | 0:100 |

Example 9

Figure 4:
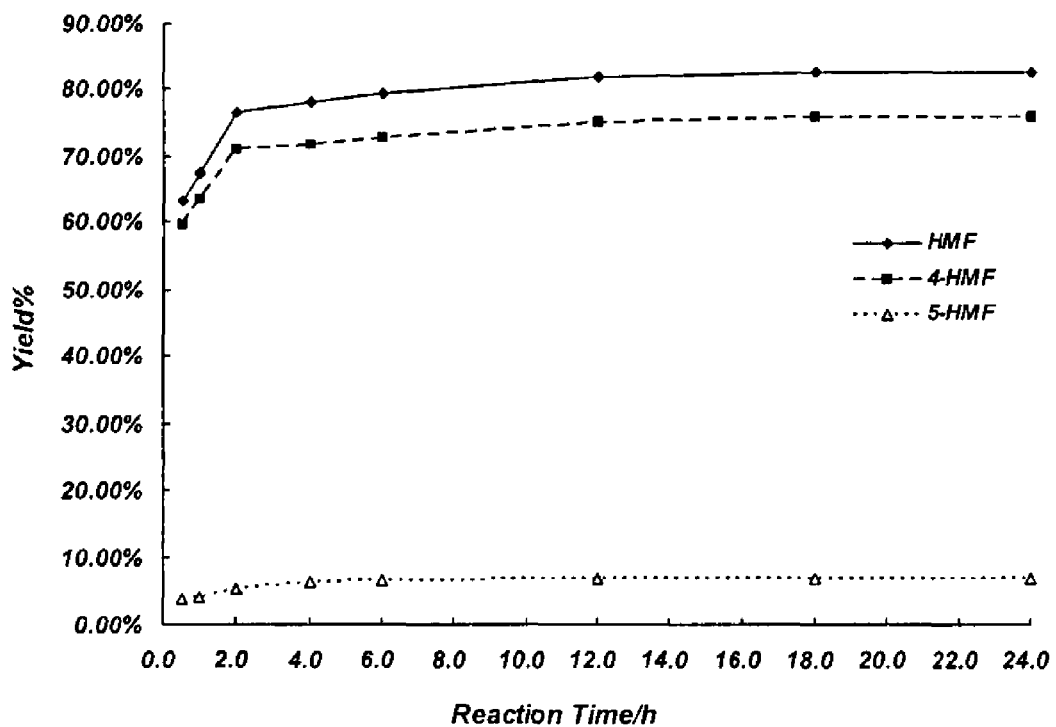
FIG. 4 is a graph showing the results of HMF yield vs. reaction time in Batch Process 1 according to an example of the invention.

This example provides a method for preparing hydroxymethylfurfural using 1,3-dihydroxyacetone (DHA) as the starting material, from which the influence of the reaction time in step b on HMF yield is obtained. The method is detailed as follows:

DHA with purity of 95% was dissolved in deionized water, and Amberlite® IRA-410 strongly basic ion exchange resin (OH form, 0.4 g) was added in the resulting solution. The reaction was allowed to proceed at 20.0° C. under agitation for a certain period of time, followed by filtration. The resin was washed with a small amount of water and 50% acetic acid solution, and the washing solution was combined with the filtrate. The filtrate was concentrated to dry under reduced pressure. To the concentrate were added DMSO (2 mL) and Amberlyst® 15 strongly acidic ion exchange resin (H form, 0.2 g). The resulting mixture was allowed to react at 110° C. under agitation for 5 hours, after which HPLC analysis was made. The results of HMF yield and product composition ratio vs. reaction time in step b was shown in FIG. 4.

Examples 10~20

Figure 5:
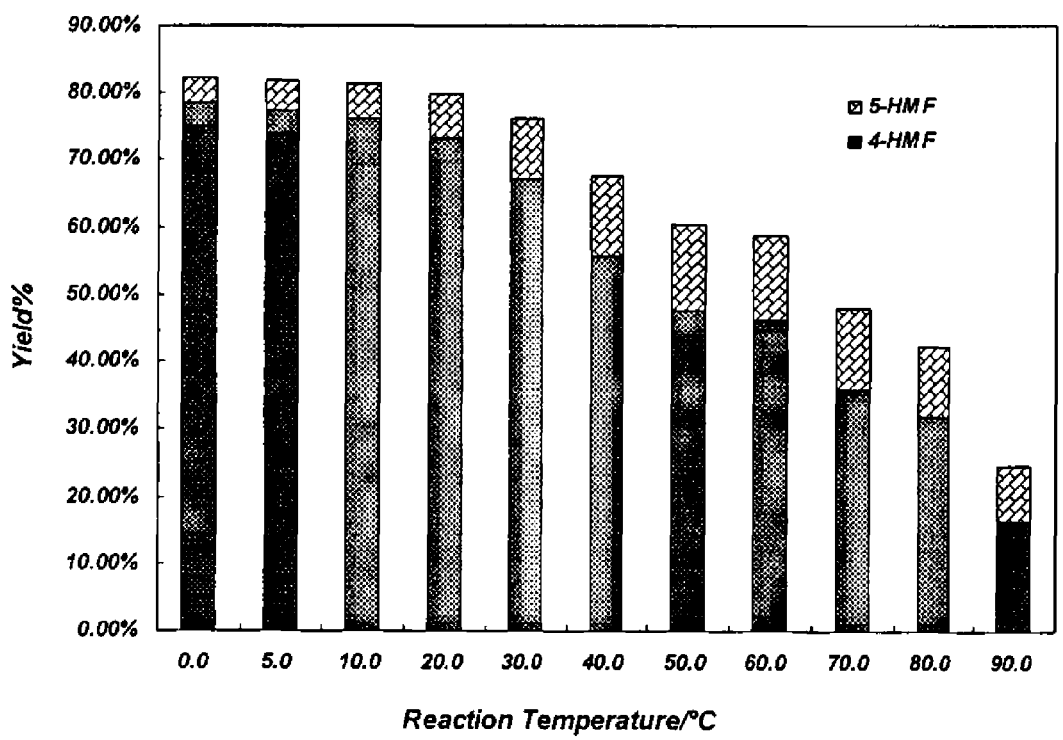
FIG. 5 is a chart showing the results of HMF yield as well as the ratio of 4-HMF to 5-HMF vs. reaction temperature in Batch Process 1 according to an example of the invention.

These examples provide a method for preparing hydroxymethylfurfural, from which the influence of the reaction temperature in step b on HMF yield and on the ratio between 4-HMF and 5-HMF in the resulting products can be seen. The details are as follows:

DHA with purity of 95% was dissolved in deionized water (4 mL), and Amberlite® IRA-410 strongly basic ion exchange resin (OH form, 0.4 g) was added in the resulting solution. The reaction was allowed to proceed at various temperatures (0° C., 5° C., 10° C., 20° C., 30° C., 40° C., 50° C., 60° C., 70° C., 80° C., 90° C. for Examples 10~20, respectively) under agitation for 12 hours, followed by filtration. The resin was washed with a small amount of water and 50% acetic acid solution, and the washing solution was combined with the filtrate. The filtrate was concentrated to dry under reduced pressure. To the concentrate were added DMSO (2 mL) and Amberlyst® 15 strongly acidic ion exchange resin (H form, 0.2 g). The resulting mixture was allowed to react at 110° C. under agitation for 5 hours, after which HPLC analysis was made. The results of HMF yield and product composition ratio vs. reaction temperature in step b was shown in Table 2 and FIG. 5.

TABLE 2

HMF yield and product composition ratio vs. reaction temperature in step b

| Example | Reaction temperature/ ° C. | 4-HMF yield | 5-HMF yield | 4-HMF: 5-HMF | Total yield |
|---|---|---|---|---|---|
| 10 | 0.0 | 78.5% | 3.8% | 95.4:4.6 | 82.3% |
| 11 | 5.0 | 77.4% | 4.4% | 94.6:5.4 | 81.8% |
| 12 | 10.0 | 76.2% | 5.0% | 93.8:6.2 | 81.2% |
| 13 | 20.0 | 73.0% | 6.8% | 91.5:8.5 | 79.9% |
| 14 | 30.0 | 67.2% | 8.9% | 88.3:11.7 | 76.2% |
| 15 | 40.0 | 55.7% | 11.9% | 82.4:17.6 | 67.5% |
| 16 | 50.0 | 47.8% | 12.6% | 79.2:20.8 | 60.4% |
| 17 | 60.0 | 46.1% | 12.6% | 78.5:21.5 | 58.8% |
| 18 | 70.0 | 35.9% | 12.0% | 75.0:25.0 | 47.9% |
| 19 | 80.0 | 31.7% | 10.6% | 75.0:25.0 | 42.3% |
| 20 | 90.0 | 16.3% | 8.3% | 66.2:33.8 | 24.7% |

Examples 21~33

Figure 6:
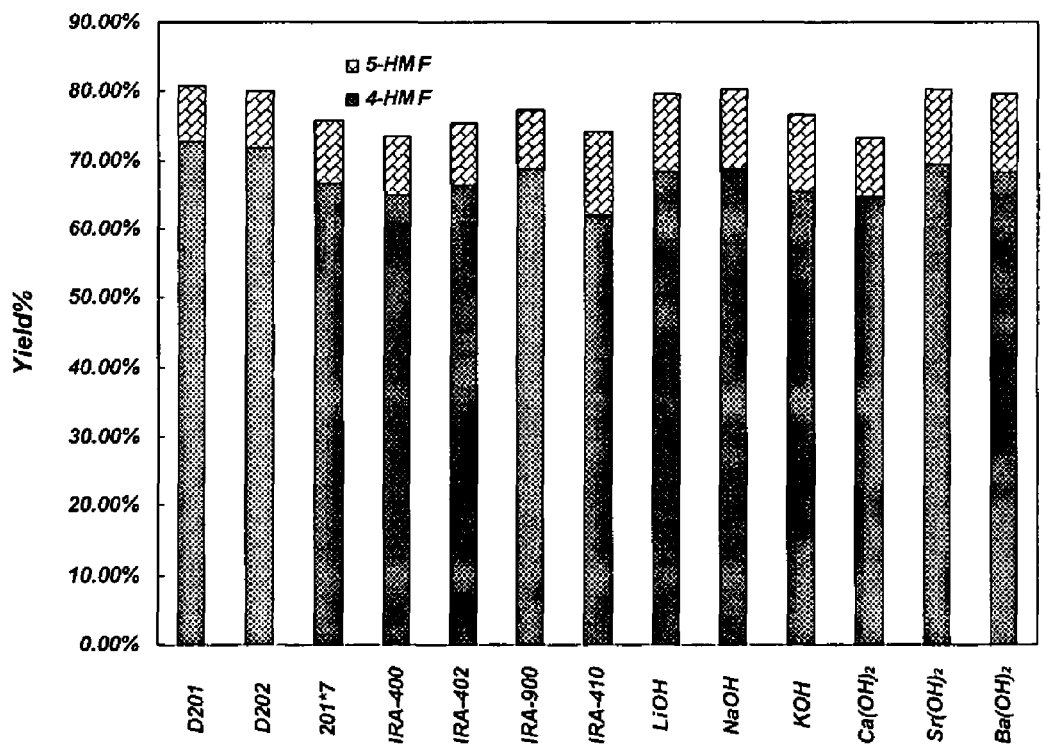
FIG. 6 is a chart showing the results of Alkaline Catalyst 1 vs. HMF yield as well as the ratio of 4-HMF to 5-HMF according to an example of the invention.

These examples provide a method for preparing hydroxymethylfurfural (HMF) using various Catalysts 1 to carry out the catalytic reaction, from which the influence of catalyst on the composition ratio between 4-HMF and 5-HMF in the products can be seen. The details are as follows:

The preparation procedure was basically the same as in Example 3, except that Amberlite® IRA-410 strongly basic ion exchange resin in Example 3 was replaced by various catalysts 1 (D201, D202, 201*7, IRA-400, IRA-402, IRA-900, IRA-410, LiOH, NaOH, KOH, Ca(OH)$_2$, Sr(OH)$_2$, and Ba(OH)$_2$ for use as Catalysts 1 in Examples 21~33 respectively). The results of HMF yield and composition ratio between 4-HMF and 5-HMF in the products vs. Catalyst 1 was shown in Table 3 and FIG. 6.

TABLE 3

HMF yield and product composition ratio vs. Catalyst 1 in step b

| Example | Catalyst 1 | 4-HMF yield | 5-HMF yield | 4-HMF: 5-HMF | Total yield |
|---|---|---|---|---|---|
| 21 | D201 | 72.77% | 7.94% | 90.2:9.8 | 80.72% |
| 22 | 202 | 71.71% | 8.29% | 89.6:10.4 | 80.01% |
| 23 | 201*7 | 66.60% | 9.21% | 87.8:12.2 | 75.80% |
| 24 | IRA-400 | 65.1% | 8.4% | 88.5:11.5 | 73.5% |
| 25 | IRA-402 | 66.3% | 9.1% | 88.0:12.0 | 75.4% |
| 26 | IRA-900 | 68.7% | 8.5% | 88.9:11.1 | 77.3% |
| 27 | IRA-410 | 61.9% | 12.3% | 83.5:16.5 | 74.2% |
| 28 | LiOH | 68.3% | 11.4% | 85.7:14.3 | 79.7% |
| 29 | NaOH | 68.7% | 11.5% | 85.7:14.3 | 80.2% |
| 30 | KOH | 65.5% | 11.1% | 85.5:14.5 | 76.6% |
| 31 | Ca(OH)$_2$ | 64.7% | 8.4% | 88.5:11.5 | 73.1% |
| 32 | Sr(OH)$_2$ | 69.4% | 10.9% | 86.4:13.6 | 80.3% |
| 33 | Ba(OH)$_2$ | 68.4% | 11.2% | 86.0:14.0 | 79.5% |

Examples 34~45

Figure 7:
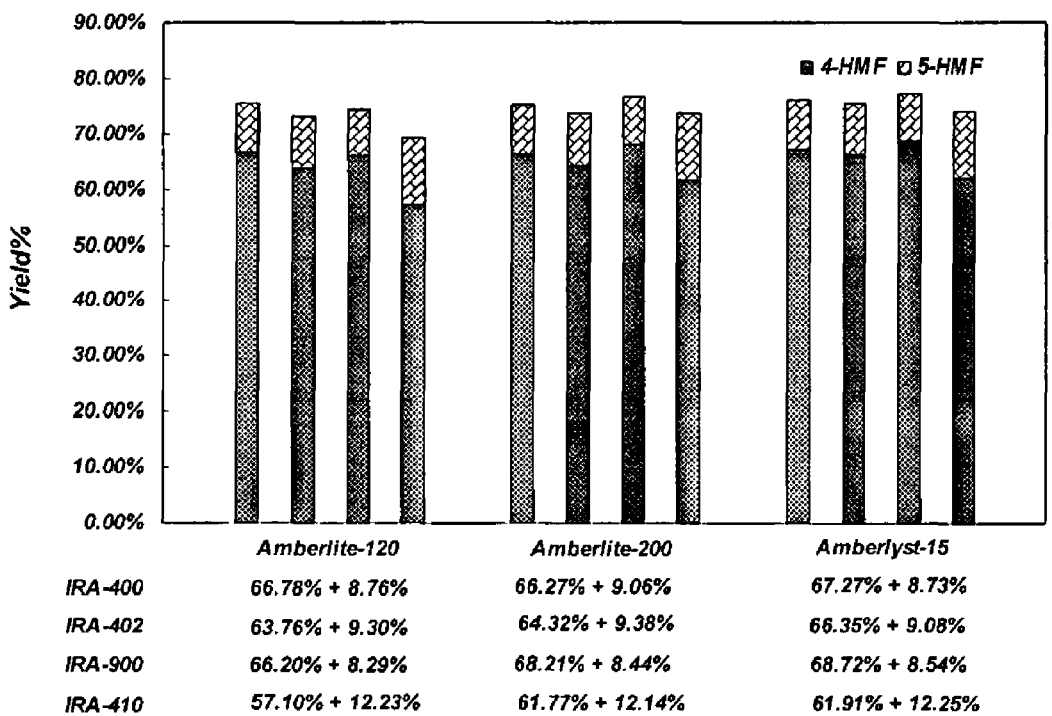
FIG. 7 is a chart showing the results of Alkaline Catalyst 1 and Acidic Catalyst 2 vs. HMF yield as well as the ratio of 4-HMF to 5-HMF according to an example of the invention.

These examples provide a method for preparing hydroxymethylfurfural (HMF) using various Catalysts 1 and Catalysts 2 to carry out the catalytic reaction, from which the influence on the composition ratio between 4-HMF and 5-HMF in the products can be seen. The details are as follows:

The preparation procedure was basically the same as in Example 3, except that Amberlite® IRA-410 strongly basic ion exchange resin was replaced by different Alkaline Catalysts 1 (IRA-400, IRA-402, IRA-900, and IRA-410 for use as Alkaline Catalysts 1 in Examples 34~45 respectively), and Amberlyst® 15 strongly acidic ion exchange resin in Example 3 was replaced by different Acidic Catalysts 2 (IR-120 for use as Acidic Catalysts 2 in Examples 34~37; IR-200 for use as Acidic Catalysts 2 in Examples 38~41; Amberlyst®15 for use as Acidic Catalysts 2 in Examples 42~45). The results of HMF yield and product composition ratio vs. Catalysts 1 and 2 was shown in FIG. 7.

Examples 46

This example provides a method for preparing hydroxymethylfurfural, particularly a method for preparing hydroxymethylfurfural (HMF) using a mixture of 1,3-dihydroxyactone (DHA) and glyceraldehyde acetonide as the starting material. The method is detailed as follows:

Glyceraldehyde acetonide with purity of 98% (0.2950 g) and 1,3-dihydroxyactone (0.2000 g) were dissolved in dimethyl sulfoxide (DMSO) (2.0 mL). To the resulting solution was added D201 macroporous strongly basic ion exchange resin (OH form, 0.4 g), and the reaction was allowed to proceed at 26° C. under agitation for 1 hour, followed by filtration to remove D201 macroporous strongly basic ion exchange resin (OH form). To the filtrate was added 001×7 strongly acidic ion exchange resin (H form, 0.2 g), and the reaction was allowed to proceed at 110° C. under agitation for 5 hours, followed by HPLC analysis which showed that the molar yield of hydroxymethylfurfural (HMF) was 23% (based on glyceraldehyde acetonide).

While only glyceraldehyde acetonide was used as a triose derivative for the starting material in this example of the invention to demonstrate the preparation method of the invention, those skilled in the art can predict, according to the idea recorded and provided in the specification, that any triose derivative that meets the requirements may be used to carry out the method in the examples of the invention for preparing hydroxymethylfurfural. In this view, no other examples in which other triose derivatives would be used as the starting material to prepare hydroxymethylfurfural will be listed here.

Examples 47~61

These examples provide a method for preparing hydroxymethylfurfural (HMF) using various Catalysts 2 to carry out the catalytic reaction, from which the influence on the composition ratio between 4-HMF and 5-HMF in the products and on the total separation recovery of hydroxymethylfurfural can be seen. The details are as follows:

DHA with purity of 95% (0.4 g) was dissolved in deionized water, and Amberlite® IRA-410 strongly basic ion exchange resin (OH form, 0.4 g) was added in the resulting solution. The reaction was allowed to proceed at 0° C. under agitation for 24 hours, followed by filtration. The resin was washed with a small amount of water and 50% acetic acid solution, and the washing solution was combined with the filtrate. The filtrate was concentrated to dry under reduced pressure. To the concentrate were added 1-ethyl-3-methylimidazole bromide ([EMIM]Br) (4 g) and lanthanide chloride salt (5 mol %). The resulting mixture was allowed to react at 100° C. under agitation for 3 hours, after which the composition ratio of the products was analyzed by HPLC. The mixture was separated by extraction with ethyl acetate, and the results of HMF separation recovery and product composition ratio vs. Catalyst 2 in step d was shown in Table 4.

TABLE 4

HMF separation recovery and product composition ratio vs. Catalyst 2 in step d

| Example | Catalyst 2 | 4-HMF yield | 5-HMF yield | 4-HMF: 5-HMF | Total yield |
|---|---|---|---|---|---|
| 47 | $YCl_3$ $6H_2O$ | 65.8% | 3.7% | 94.6:5.4 | 69.5% |
| 48 | $LaCl_3$ $6H_2O$ | 64.8% | 3.8% | 94.5:5.5 | 68.6% |
| 49 | $CeCl_3$ $6H_2O$ | 64.9% | 3.7% | 94.6:5.4 | 68.6% |
| 50 | $PrCl_3$ $6H_2O$ | 61.6% | 3.6% | 94.5:5.5 | 65.2% |
| 51 | $NdCl_3$ $6H_2O$ | 66.5% | 3.9% | 94.4:5.6 | 70.5% |
| 52 | $SmCl_3$ $6H_2O$ | 62.1% | 3.7% | 94.4:5.6 | 65.8% |
| 53 | $EuCl_3$ $6H_2O$ | 64.4% | 4.0% | 94.2:5.8 | 68.4% |
| 54 | $GdCl_3$ $6H_2O$ | 63.6% | 3.5% | 94.8:5.2 | 67.0% |
| 55 | $TbCl_3$ $6H_2O$ | 62.6% | 3.3% | 95.0:5.0 | 65.8% |
| 56 | $DyCl_3$ $6H_2O$ | 69.2% | 3.7% | 94.9:5.1 | 72.9% |
| 57 | $HoCl_3$ $6H_2O$ | 69.3% | 4.6% | 93.8:6.2 | 73.8% |
| 58 | $ErCl_3$ $6H_2O$ | 70.2% | 3.4% | 95.3:4.7 | 73.6% |
| 59 | $TmCl_3$ $6H_2O$ | 69.3% | 3.8% | 94.8:5.2 | 73.1% |
| 60 | $YbCl_3$ $6H_2O$ | 68.4% | 4.2% | 94.2:5.8 | 72.5% |
| 61 | $LuCl_3$ $6H_2O$ | 66.4% | 3.2% | 95.4:4.6 | 69.6% |

Examples 62~66

These examples provide a method for preparing hydroxymethylfurfural (HMF) using Continuous Process 1 in step b at various liquid hourly space velocities (LHSV), from which the influence on the composition ratio between 4-HMF and 5-HMF in the products and on the total separation recovery of hydroxymethylfurfural can be seen. The details are as follows:

A jacket glass tube (inner tube: L=382 mm, id=10 mm, V=30 mL) was used as a stationary catalyst bed. The inner tube was filled with IRA-900 strongly basic resin, and circulating cooling was exerted by the jacket using a cooling liquid having a temperature of −2° C. An aqueous solution of 10% DHA was made to pass through the stationary catalyst bed at a certain flow rate using a liquid phase pump. The reaction solution obtained was concentrated to dry under reduced pressure. An amount of concentrate (0.4 g) was added to DMSO (2 mL), and then Amberlyst® 15 strongly acidic ion exchange resin (H form, 0.2 g) was added. After the mixture was allowed to react at 110° C. under agitation for 5 hours, HPLC analysis was carried out. The results of HMF yield and product composition ratio vs. liquid hourly space velocity in Continuous Process 1 of step b was shown in Table 5.

TABLE 5

HMF yield and product composition ratio vs. liquid hourly space velocity in Continuous Process 1 of step b

| Example | Liquid hourly space velocity ($h^{-1}$) | 4-HMF recovery | 5-HMF recovery | 4-HMF: 5-HMF | Total HMF recovery |
|---|---|---|---|---|---|
| 62 | 0.5 | 80.4% | 5.8% | 93.3:6.7 | 86.2% |
| 63 | 1.0 | 78.7% | 4.9% | 94.1:5.9 | 83.6% |
| 64 | 2.0 | 72.0% | 4.0% | 94.8:5.2 | 76.0% |
| 65 | 3.0 | 52.9% | 2.3% | 95.8:4.2 | 55.2% |
| 66 | 5.0 | 33.4% | 1.3% | 96.1:3.9 | 34.8% |

Examples 67~72

These examples provide a method for preparing hydroxymethylfurfural (HMF) using Continuous Process 2 in step d at various liquid hourly space velocities (LHSV), from which the influence on the composition ratio between 4-HMF and 5-HMF in the products and on the total separation recovery of hydroxymethylfurfural can be seen. The details are as follows:

A jacket glass tube (inner tube: L=382 mm, id=10 mm, V=30 mL) was used as a stationary catalyst bed. The inner tube was filled with IRA-900 strongly basic resin, and circulating cooling was exerted by the jacket using a cooling liquid having a temperature of −2° C. An aqueous solution of 10% DHA was made to pass through the stationary catalyst bed at a specific flow rate (1.0 $h^{-1}$) using a liquid phase pump. The reaction solution obtained was concentrated to dry under reduced pressure, resulting in a branched ketose. A stainless steel tube (L=191 mm, id=10 mm, V=15 mL) was used as a stationary catalyst bed and was filled with Amberlyst-15 strongly acidic resin. The above branched ketose was dissolved in DMSO (10% solution of the branched saccharide in DMSO) and then passed at a certain flow rate through the stationary catalyst bed at 110° C. HPLC analysis. The results of HMF yield and product composition ratio vs. liquid hourly space velocity in the Continuous Process 2 of step d was shown in Table 6.

TABLE 6

HMF yield and product composition ratio vs. liquid hourly space velocity in Continuous Process 2 of step d

| Example | Liquid hourly space velocity ($h^{-1}$) | 4-HMF recovery | 5-HMF recovery | 4-HMF: 5-HMF | Total HMF recovery |
|---|---|---|---|---|---|
| 67 | 1.0 | 79.6% | 4.0% | 95.2:4.8 | 83.6% |
| 68 | 2.0 | 80.2% | 4.0% | 95.2:4.8 | 84.2% |
| 69 | 3.0 | 80.0% | 3.9% | 95.3:4.7 | 83.9% |
| 70 | 4.0 | 78.1% | 3.8% | 95.4:4.6 | 81.9% |
| 71 | 5.0 | 78.0% | 3.6% | 95.6:4.4 | 81.6% |
| 72 | 6.0 | 76.4% | 3.4% | 95.7:4.3 | 79.8% |

Example 73

This example provides a method for preparing hydroxymethylfurfural, particularly a method for preparing 4-hydroxymethylfurfural (4-HMF) via Continuous Process 1 in step b and Continuous Process 2 in step d using 1,3-dihydroxyactone (DHA) as the starting material, followed by separating 4-hydroxymethylfurfural (4-HMF) by column chromatography. The method is detailed as follows:

A jacket glass tube (inner tube: L=382 mm, id=10 mm, V=30 mL) was used as a stationary catalyst bed. The inner tube was filled with IRA-900 strongly basic resin, and circulating cooling was exerted by the jacket using a cooling liquid having a temperature of −2° C. An aqueous solution of 10% DHA was made to pass through the stationary catalyst bed at a specific flow rate (1.0 $h^{-1}$) using a liquid phase pump. The reaction solution obtained was concentrated to dry under reduced pressure, resulting in a branched ketose. A stainless steel tube (L=191 mm, id=10 mm, V=15 mL) was used as a stationary catalyst bed and was filled with Amberlyst-15 strongly acidic resin. The above branched ketose was dissolved in DMSO (10% solution of the branched saccharide in DMSO) and then passed at a specific flow rate (2.0 $h^{-1}$) through the stationary catalyst bed at 110° C. Most of the solvent DMSO was removed from the resulting mixture by distillation under reduced pressure at a temperature 50° C. Then, a saturated aqueous solution of $NaHCO_3$ was added, followed by successive extraction with $CH_2Cl_2$. After concentrated, the extract was subjected to column chromatography, wherein it was eluted with petroleum ether/ethyl acetate=1/1, resulting in a separation recovery of 80%. The product composition ratio obtained by HPLC analysis was 4-HMF:5-HMF≧99.5:0.5.

Example 74

This example provides a method for preparing hydroxymethylfurfural, particularly a method for preparing 4-hydroxymethylfurfural (4-HMF) via Continuous Process 1 in step b and Continuous Process 2 in step d using 1,3-dihydroxyactone (DHA) as the starting material, followed by separating 4-hydroxymethylfurfural (4-HMF) by distillation under reduced pressure. The method is detailed as follows:

A jacket glass tube (inner tube: L=382 mm, id=10 mm, V=30 mL) was used as a stationary catalyst bed. The inner tube was filled with IRA-900 strongly basic resin, and circulating cooling was exerted by the jacket using a cooling liquid having a temperature of −2° C. An aqueous solution of 10% DHA was made to pass through the stationary catalyst bed at a specific flow rate (1.0 $h^{-1}$) using a liquid phase pump. The reaction solution obtained was concentrated to dry under reduced pressure, resulting in a branched ketose. A stainless steel tube (L=191 mm, id=10 mm, V=15 mL) was used as a stationary catalyst bed. The stainless steel tube was filled with Amberlyst-15 strongly acidic resin. The above branched ketose was dissolved in DMSO (10% solution of the branched saccharide in DMSO) and then passed at a specific flow rate (2.0 $h^{-1}$) through the stationary catalyst bed at 110° C. Most of the solvent DMSO was removed from the resulting mixture by distillation under reduced pressure at a temperature 50° C. Then, a saturated aqueous solution of $NaHCO_3$ was added, followed by successive extraction with $CH_2Cl_2$. After concentrated, the extract was subjected to distillation under reduced pressure, resulting in a separation recovery of 60%. The product composition ratio obtained by HPLC analysis was 4-HMF:5-HMF≧95:5.

In summary, according to the examples of the invention, an aldotriose used as a starting material is subjected to catalytic condensation (aldol condensation) to give a linear hexose which is then subjected to catalytic dehydration in a way similar to fructose to give 5-hydroxymethylfurfural (HMF); or a ketotriose used as a starting material is subjected to catalytic condensation (aldol condensation) to give a branched hexose which is then subjected to catalytic dehydration in a way similar to fructose to give 4-hydroxymethylfurfural (HMF). As this method is characterized by simple process, convenient preparation, easy separation, and triose is abundant and cheap, the manufacturing cost of 5-hydroxymethylfurfural (HMF) is lowered effectively, and the problem encountered in conventional methods for preparing 5-hydroxymethylfurfural (HMF) that the starting materials used are all derived from sucrose or starch, the major food of human beings, is avoided, so that the consumption of food as the starting material for preparing 5-hydroxymethylfurfural (HMF) will be reduced, and its impact on the deteriorating food crisis will be alleviated. Meanwhile, the composition ratio between 4-hydroxymethylfurfural and 5-hydroxymethylfurfural can be controlled selectively by selection of the starting material, the reaction temperature in step b and Catalyst 1. In addition, a new synthesis route is established for 4-hydroxymethylfurfural.

What have been described above are only some preferred specific embodiments of the invention. The protection scope of the invention is not limited to these embodiments, nor is it limited to the order of the various embodiments in any way. Any change or alternative apparent to any one skilled in the art, within the technical scope disclosed by the invention, is intended to be included in the protection scope of the invention. Therefore, the protection scope of the invention should be defined by the protection scope of the claims.

The invention claimed is:

1. A method for preparing hydroxymethylfurfural comprising the steps of:

a. dissolving a triose in Solvent 1 to obtain a first reaction mixture, wherein the triose used in said method refers to a single compound having structural feature (III) or (IV), or a mixture thereof:

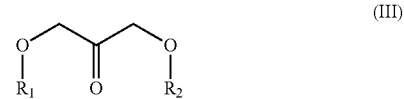

(III)

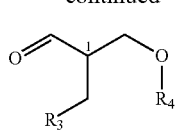

wherein, in the above formulae (III) and (IV), $R_1$, $R_2$, $R_3$ and $R_4$ each independently represents H, —PO(OH)$_2$, $C_1$-$C_6$alkylcarbonyloxy or $C_{1-6}$alkyl or alkyl containing 1~6 carbon atoms; alternatively, $R_1$ and $R_2$ taken together; and $R_3$ and $R_4$ taken together, represent ketal formula Va or Vb; or $R_1$ and $R_2$ taken to ether taken together represents ketal formula Va or Vb, while each substituent in $R_3$ and $R_4$ independently represents H, —PO(OH)$_2$, $C_1$-$C_6$alkylcarbonyloxy or $C_{1-6}$alkyl or alkyl containing 1~6 carbon atoms; or $R_3$ and $R_4$ taken together represents ketal formula Va or Vb while each substituent in $R_1$ and $R_2$ independently represents H, —PO(OH)$_2$, $C_1$-$C_6$alkylcarbonyloxy or $C_{1-6}$alkyl or alkyl containing 1-6 carbon atoms; alternatively, $R_1$, $R_2$, $R_3$, and $R_4$ independently has the following structural feature (V),

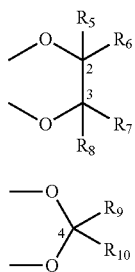

wherein in the above formula (V), $R_5$, $R_6$, $R_7$ and $R_8$ each independently represents H or $C_1$-$C_6$alkyl, and $R_9$ and $R_{10}$ each independently represents H or $C_1$-$C_6$alkyl; and the chiral configuration of $C_1$ in formula (IV) isomers thereof, and the chiral configurations of C2, C3 and C4 in formula V isomers thereof, and wherein Solvent 1 is any one or any combination of water, dimethyl sulfoxide, dimethyl formamide, dimethyl acetylamide, methylene dichloride, tetrahydrofuran, 1,4-dioxane, N-methyl pyrrolidinone, acetonitrile, cyclobutyl sulfone, trimethyl phosphate, and ethyl acetate;

b. adding Alkaline Catalyst 1 into the first reaction mixture to make a reaction occur under agitation at a temperature of −40~100° C. to obtain a hexose by condensation, wherein Alkaline Catalyst 1 is any one of Bronsted bases, Lewis bases, metal complexes, amino acids, and ion exchange resins;

c. dissolving the condensation product hexose in Solvent 2 to obtain a second reaction mixture, wherein Solvent 2 is any one or an combination of dimethyl sulfoxide, dimethyl formamide, dimethyl acetylamide, N-methyl pyrrolidinone, tetramethylurea, cyclobutyl sulfone, trimethyl phosphate, and methyl propyl ketone;

d. adding Acidic Catalyst 2 into the second reaction mixture, and heating the second reaction mixture with Acidic Catalyst 2 therein at a temperature of 80~280° C. which is sufficient to form hydroxymethylfurfural, to obtain a third mixture containing said hydroxymethylfurfural, wherein Acidic Catalyst 2 is any one of Bronsted acids, Lewis acids, metal complexes, solid acids, heteropoly acids and ion exchange resins; wherein said hydroxymethylfurfural is a single compound having structural feature (I) or (II), or a mixture thereof

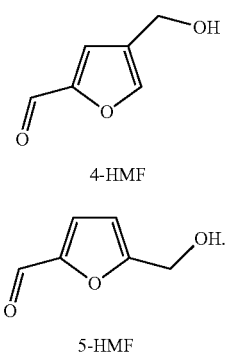

2. The method for preparing hydroxymethylfurfural according to claim 1, wherein said step b
is carried out by passing the first reaction mixture at a certain flow rate through a stationary catalyst bed loaded with Alkaline Catalyst 1 at a reaction temperature of −40~100° C.

3. The method for preparing hydroxymethylfurfural according to claim 1, wherein said step d is carried out
by passing the second reaction mixture at a certain flow rate through a stationary catalyst bed loaded with Acidic Catalyst 2 at a reaction temperature of 80~280° C.

4. The method for preparing hydroxymethylfurfural according to claim 1, wherein said method further comprises:
e. separating and purifying the third mixture containing hydroxymethylfurfural by liquid-liquid extraction, or distillation under reduced pressure, or column chromatography to obtain hydroxymethylfurfural.

5. The method for preparing hydroxymethylfurfural according to claim 1, wherein, when a triose or its derivative having structural feature (III) is used as the starting material in said method, by using basic ion exchange resin as Alkaline Catalyst 1 in said step b, the ratio between compound 4-hydroxymethylfurfural having structural feature (I) and compound 5-hydroxymethylfurfural having structural feature (II) in the resulting products is adjusted to be 4-hydroxymethylfurfural:5-hydroxymethylfurfural=99:1~1:1.

6. The method for preparing hydroxymethylfurfural according to claim 1, wherein the hexose obtained in said step b by condensation is a linear hexose and/or a branched hexose, wherein
said linear hexose is any one or any combination of glucose, galactose, mannose, allose, altrose, gulose, talose, idose, fructose, sorbose, tagatose, psicose, their ethers, ethers and optical isomers thereof; and
said branched hexose is any one or any combination of dendroketose, its ethers and ethers thereof, and their optical isomers.

7. The method for preparing hydroxymethylfurfural according to claim 1, wherein said method further comprises removing said Catalyst 1 and said Solvent 1 from said condensation product hexose obtained in said step b before said step c.

8. The method for preparing hydroxymethylfurfural according to claim 1, wherein the reaction temperature in said step b is 0~60° C.

9. The method for preparing hydroxymethylfurfural according to claim 1, wherein the heating temperature in said step d for forming hydroxymethylfurfural is 100~180° C.

10. The method for preparing hydroxymethylfurfural according to claim 2, wherein said step b of passing the first reaction mixture at a certain flow rate through a stationary catalyst bed loaded with Alkaline Catalyst 1 at a reaction temperature of −40~100° C. comprises:
passing the first reaction mixture at a liquid hourly space velocity of 0.1~10.0 h−1 through a stationary catalyst bed loaded with an Alkaline Catalyst 1 at a reaction temperature of −40–100° C.

11. The method for preparing hydroxymethylfurfural according to claim 3, wherein said step d of passing the second reaction mixture at a certain flow rate through a stationary catalyst bed loaded with Acidic Catalyst 2 at a reaction temperature of 80~280° C. comprises:
passing the second reaction mixture at a liquid hourly space velocity of 0.1~10.0 h−1 through a stationary catalyst bed loaded with Acidic Catalyst 2 at a reaction temperature of 80~100° C.

12. The method for preparing hydroxymethylfurfural according to claim 1, wherein said step d comprises:
obtaining hydroxymethylfurfural from the third mixture containing hydroxymethylfurfural by liquid-liquid extraction, or distillation under reduced pressure when an ionic liquid is used as Solvent 2 in step c for obtaining the second reaction mixture by dissolution, wherein the extracting agent is an organic solvent immiscible with the ionic liquid system and is any one or any combination of ethyl acetate, ethyl ether, methylene dichloride and chloroform; or
obtaining hydroxymethylurfural from the third mixture containing hydroxymethylfurfural by distillation under reduced pressure, or column chromatography when a non-ionic liquid is used as Solvent 2 in step c for obtaining the second reaction mixture by dissolution.

13. The method for preparing hydroxymethylfurfural according to claim 1, wherein, in said method, when a compound of triose having structural feature (III) is used as the starting material, the resulting product comprises compound 4-hydroxymethylfurfural having structural feature (I).

14. The method for preparing hydroxymethylfurfural according to claim 1, wherein, in said method, when a compound of triose having structural feature (IV) is used as the starting material, the resulting product comprises compound 5-hydroxymethylfurfural having structural feature (II).

15. The method for preparing hydroxymethylfurfural according to claim 1, wherein, in said method, when a mixture of a compound of triose having structural feature (III) and a compound of triose having structural feature (IV) is used as the starting material, the resulting product comprises a mixture of 4-hydroxymethylfurfural having structural feature (I) and 5-hydroxymethylfurfural having structural feature (II).

16. The method for preparing hydroxymethylfurfural according to claim 1, wherein when the reaction temperature is in the range of −40~25° C. in said step b, the ratio between compound 4-hydroxymethylfurfural having structural feature (I) and compound 5-hydroxymethylfurfural having structural feature (II) in the resulting products is 4-hydroxymethylfurfural:5-hydroxymethylfurfural=99:1~9:1.

17. The method for preparing hydroxymethylfurfural according to claim 1, wherein when the reaction temperature is in the range of 25~100° C. in said step b, the ratio between compound 4-hydroxymethylfurfural having structural feature (I) and compound 5-hydroxymethylfurfural having structural feature (II) in the resulting products is 4-hydroxymethylfurfural:5-hydroxymethylfurfural=9:1~2:1.

* * * * *